(12) United States Patent
Mukherjee et al.

(10) Patent No.: US 9,180,212 B2
(45) Date of Patent: Nov. 10, 2015

(54) β-AMYLOID PLAQUE IMAGING AGENTS

(71) Applicant: The Regents of the University of California, Oakland, CA (US)

(72) Inventors: Jogeshwar Mukherjee, Irvine, CA (US); Min-Liang Pan, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/899,985

(22) Filed: May 22, 2013

(65) Prior Publication Data

US 2013/0315826 A1    Nov. 28, 2013

Related U.S. Application Data

(60) Provisional application No. 61/650,053, filed on May 22, 2012.

(51) Int. Cl.
    *A61K 51/00*    (2006.01)
    *A61K 51/04*    (2006.01)

(52) U.S. Cl.
    CPC ..................................... *A61K 51/04* (2013.01)

(58) Field of Classification Search
    CPC ... A61K 51/00; A61K 51/04; A61K 51/0455; A61K 51/0459
    USPC ............ 424/1.11, 9.3, 9.6, 1.89; 544/60, 162, 544/382
    See application file for complete search history.

(56) References Cited

U.S. PATENT DOCUMENTS

2003/0138374 A1*  7/2003  Kudo et al. .................. 424/1.11
2006/0269473 A1* 11/2006  Kung et al. .................. 424/1.11

OTHER PUBLICATIONS

Kung, Hank F et al; F Stilbenes and Styrylpyridines for PET IMaging of AB PLaques in Alzheimer's Disease: A Miniperspective; J. Med. Chem. 2010, 53, 933-341.

* cited by examiner

*Primary Examiner* — Michael G Hartley
*Assistant Examiner* — Jagadishwar Samala
(74) *Attorney, Agent, or Firm* — Fish & Tsang, LLP

(57) ABSTRACT

Various compounds, compositions, and methods for binding to β-amyloid plaque and norepinephrine transporters are presented. Especially preferred compounds include those with a PET-detectable label.

8 Claims, 8 Drawing Sheets

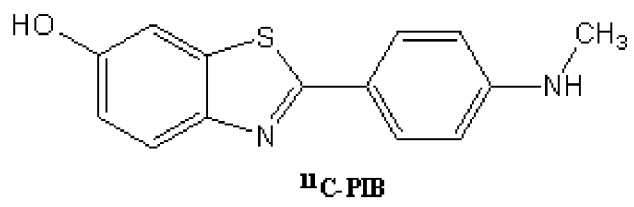
Prior Art Figure 1A
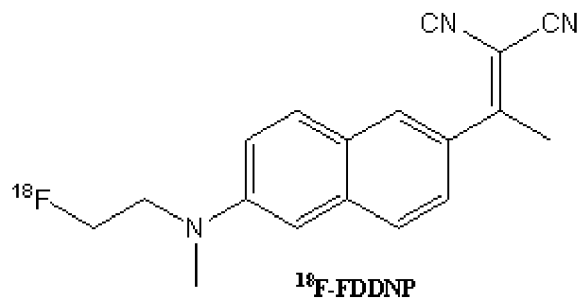
Prior Art Figure 1B
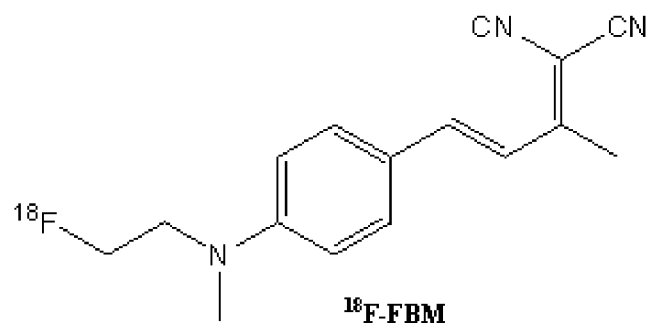
Prior Art Figure 1C

β-AMYLOID PLAQUE IMAGING AGENTS

This application claims priority to our U.S. provisional application having Ser. No. 61/650,053, which was filed May 22, 2013.

This invention was made with Government support under Grant No. AG029479 awarded by the National Institutes of Health. The Government has certain rights in this invention.

FIELD OF THE INVENTION

The field of the invention is pharmaceutical compositions and methods therefore, and especially as it relates to compositions and methods of labeling and/or imaging of beta amyloid plaque and/or norepinephrine transporters.

BACKGROUND

The following description includes information that may be useful in understanding the present invention. It is not an admission that any of the information provided herein is prior art or relevant to the presently claimed invention, or that any publication specifically or implicitly referenced is prior art.

Alzheimer's disease (AD) is a progressive neurodegenerative condition affecting almost one in ten individuals over the age of 65, accounts for over 50% of senile dementia and the majority of pre-senile dementia cases, and is characterized by progressive deterioration of higher cognitive functions, including the loss of memory. AD is typically characterized by accumulation of β-amyloid plaques and neurofibrillary tangles (NFT) in the brain and many neurodegenerative effects of AD appear to be closely linked to amyloid production. In addition to these specific neuropathological features, AD brains exhibit extensive cellular atrophy and cell loss, shrinkage of cortical thickness, enlargement of sulci and ventricles, and changes in multiple neurochemical systems including acetylcholine (ACh), glutamate, GABA and serotonin. There is increasing effort to see if all features/symptoms of AD can be associated with the accumulation of amyloid plaques and tangles.

With increasing efforts to find treatments and a cure for AD, there is much research into imaging plaques and NFT essential to the diagnosis and clinical management of AD. More recently, various $^{18}F$ agents have been developed to enable more wide-spread use of amyloid PET imaging, and efforts are currently underway for the development and evaluation of NFT PET imaging agents.

For example, one class of PET imaging agents comprises substituted aminonaphthalene backbones that have been shown to target the polymeric form of the β-amyloid peptide that is associated with senile plaques and bind to neurofibrillary tangles. Most prominently, 2-(1-{6-[(2-[$^{18}F$]fluoroethyl)(methyl)amino]-2-naphtyl}ethylidene)malonitrile (known as [$^{18}F$]FDDNP), became the first diagnostic tool to image plaques and tangles with relatively high specificity (see e.g., U.S. Pat. Nos. 6,274,119 and 6,660,530). Further related compounds are described in U.S. Pat. App. No. 2007/0053831. However, [$^{18}F$]FDDNP is highly lipophilic and consequently exhibits some nonspecific binding. Therefore, the results obtained from PET scans using [$^{18}F$]FDDNP are often relatively poor in image quality and make diagnosis difficult. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

Still other known labeling compounds include numerous substituted and radiolabeled benzofuran compounds as described, for example, in U.S. Pat. No. 7,173,061, and numerous substituted quinolinehydrazones as described, for example, in U.S. Pat. No. 6,589,504. Various substituted phenyl imidazo[1,2-b]pyridazine and similar structures are described as imaging agents in WO 2007/033080, and selected substituted benzathiazole compounds are known for labeling and are described in WO 2007/035405. Still further known compounds with more or less specific binding to amyloid are referred to in U.S. Pat. App. No. 2005/0048000. However, and similarly to FDDNP, such known compounds are often problematic with respect to their transport across the blood-brain barrier, stability under physiological conditions, and selectivity towards neurofibrillary tangles and/or senile plaques.

Significant advances have been made in plaque imaging, for example using $^{11}C$-PIB, and Prior Art FIG. 1A depicts the chemical structure of $^{11}C$-PIB. However, little PIB binding was seen in PS1/APP transgenic mice brain despite the substantial amount of Aβ plaques using $^{11}C$-PIB. More recently, microPET imaging in APP23 transgenic mice has yielded better results on Aβ-plaque localization using high specific activity $^{11}C$-PIB. Thus, there is continued interest in the further development of Aβ-plaque imaging agents. Among those are imaging agents that are labeled with fluorine-18, which may provide a higher target to non-target ratio. For example, such agents include $^{18}F$-Florbetapir, $^{18}F$-Flutmetamol, and $^{18}F$-Florbetaben.

Likewise, advances have also been made in tangle imaging agents. For example, the first agent developed was fluorine-18 labeled FDDNP which is being used for imaging plaques and tangles. $^{18}F$-FDDNP is highly lipophilic (log P>3) due to its structure, particularly the naphthalene ring which gives low target to non-target ratios. This results in poor image quality and makes diagnosis difficult; however $^{18}F$-FDDNP is currently one of the few radiotracers suitable for NFT imaging (Shin et al., 2011). Prior Art FIG. 1B depicts the chemical structure of $^{18}F$-FDDNP.

Numerous efforts are also currently underway to develop NFT imaging agents that may provide improved in vivo properties. Quinoline and benzimidazole derivatives have been reported to show selectivity for NFT. Over the past few decades traumatic brain injury (TBI) has become a major public health problem that is associated with significant medical and psychological morbidity and socioeconomic costs. Importantly, TBI from improvised explosive devices and other destructive weapons has become the signature injury of the current wars in Afghanistan and Iraq. Significant amount of resources have been allocated toward understanding the underlying basis of TBI and developing effective neuroprotective therapies, particularly for mild TBI (mTBI). However, large gaps remain in basic knowledge and ability to prevent many of the long-term consequences of mTBI. Among the major obstacles preventing progress are the lack of standardized tools for accurate diagnosis of mTBI, and to physiologically monitor the course of the disease and response to treatment. Notably, animal models of mTBI and human post-mortem brain tissue from individuals with chronic traumatic encephalopathy have established a strong link between TBI and abnormal deposition of tau protein in the brain, which is also a major pathological hallmark of Alzheimer's disease. Unfortunately, the only way to reliably evaluate the status of tau deposition in the brain currently is by post-mortem analysis.

The inventors have recently have developed FBM (4'-[(2-fluoroethyl)(methyl)amino]-4-phenyl-3-buten-2-malonitrile) for NFT imaging. The ability to image tau deposits in the brain will significantly improve the understanding of the role played by tau in the pathophysiology of TBI. Tau imaging could directly impact the detection, diagnosis and treatment of mTBI and help in further understanding AD. Prior Art FIG. 1C shows the chemical structure of $^{18}$F-FBM. However, $^{18}$F-FBM may not fully satisfy all requirements for imaging of plaque and NFT in AD. Further known imaging agents for β-amyloid plaques are disclosed in US 2003/0138374.

Thus, even though various imaging compositions and methods are known in the art, all or almost all of them suffer from one or more disadvantages. Moreover, current use of the known imaging agents is limited to β-amyloid plaques and/or neurofibrillary tangles. Therefore, there is still a need for improved compositions and methods of beta-amyloid imaging compounds and compositions.

SUMMARY OF THE INVENTION

The present invention is directed to various compositions and methods for labeling and/or treatment of neural tissues that are characterized by the presence of β-amyloid plaques, and/or the uptake of norepinephrine in the presence of a norepinephrine transporter in various tissues, and especially neural and adipose tissue.

Most preferably, contemplated compounds are those having the general structure of 'substituted amine-(hetero)aryl-linker-(hetero)aryl-substituted amine', and especially particularly preferred compounds are labeled with a PET-detectable label (e.g., $^{11}$C or $^{18}$F). Thus, and among other compounds, particularly preferred compounds include analogs and derivatives of 4,4'-diarylamines having a suitable linker between the two aryl groups (e.g., having a diazostilbene, azostilbene, or stilbene scaffold).

In one preferred aspect of the inventive subject matter, contemplated compounds have a structure according to Formula I

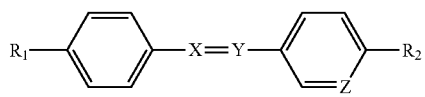

Formula I in which X and Y are independently CH or N, or taken together are C(O)NH, and in which Z is CH or N. With respect to $R_1$ it is preferred that $R_1$ is $NR_3R_4$ or $OR_5$, and it is further preferred that $R_2$ is $NR_3R_4$, halogen, halogen isotope, O-fluoroheteroaryl, or $NR_3$-fluoroheteroaryl. $R_3$, $R_4$, and $R_5$ are independently H, lower alkyl, lower fluoroalkyl, O-alkyl; O-fluoroalkyl; C(O)-alkyl, or C(O)-fluoroalkyl, and it is still further generally preferred that at least one fluorine atom is present in $R_3$, $R_4$, or $R_5$ and is an $^{18}$F atom, or that at least one carbon atom in $R_3$, $R_4$, or $R_5$ is a $^{11}$C atom.

In further preferred compounds, the fluorine atom is located in $R_3$, $R_4$, or $R_5$, for example, as $CO(CH_2)_nCH_2{}^{18}F$ or $(CH_2)_nCH_2{}^{18}F$, with n being an integer between 1 and 6. Likewise, it is preferred that the $^{11}$C atom is located in $R_3$, $R_4$, or $R_5$, for example, in an $^{11}CH_3$ or $(CH_2)_n{}^{11}CH_3$ group, with n being an integer between 1 and 6. While not limiting to the inventive subject matter, it is also preferred that X and Y are both N or both C.

Therefore, especially preferred compounds will have a structure according to Formula II, Formula III, Formula IV, or Formula V (with $R_3$ being $CO(CH_2)_nCH_2{}^{18}F$, or $(CH_2)_nCH_2{}^{18}F$, and with n being an integer between 1 and 6)

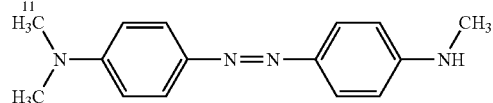

Formula II

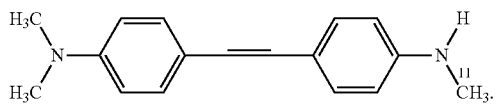

Formula III

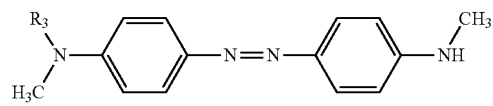

Formula IV

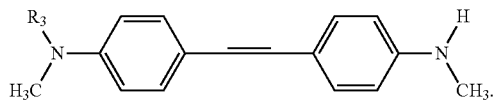

Formula V

In another preferred aspect of the inventive subject matter, the inventors also contemplate various pharmaceutical or diagnostic compositions that include one or more of the compounds presented herein, typically in conjunction with a pharmaceutically acceptable carrier. Thus, the compound in especially preferred pharmaceutical or diagnostic compositions will have at least one $^{18}$F atom in $R_3$, $R_4$, or $R_5$, and/or at least one $^{11}$C atom in $R_3$, $R_4$, or $R_5$. It is further generally preferred that the compound will be present in the composition in an amount effective to allow PET imaging of a β-amyloid plaque or neurofibrillary tangle in vitro and/or in vivo. Typically, the pharmaceutical or diagnostic compositions will be formulated for parenteral administration.

In yet another aspect of the inventive subject matter, the inventors contemplate a method of PET imaging that includes a step of contacting (most preferably in vivo) a neural tissue and/or tissue having a norepinephrine transporter with a compound having a structure of Formula I:

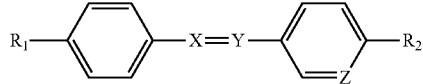

Formula I wherein X is CH or N, wherein Y is CH or N, or wherein X and Y together are C(O)NH, and wherein Z is CH or N; wherein $R_1$ is $NR_3R_4$ or $OR_5$; and wherein $R_2$ is $NR_3R_4$, halogen, halogen isotope, O-fluoroheteroaryl, or NR3-fluoroheteroaryl; wherein $R_3$, $R_4$, and $R_5$ are independently selected from the group consisting of H, lower alkyl, lower fluoroalkyl, O-alkyl; O-fluoroalkyl; C(O)-alkyl, or C(O)-fluoroalkyl; wherein at least one fluorine atom in $R_3$, $R_4$, or $R_5$ is an $^{18}$F atom, or wherein at least one carbon atom in $R_3$, $R_4$, or $R_5$ is a $^{11}$C atom. In another step, a positron emission decay is detected in the tissue to so provide imaging information, typically indicative of location and/or quantity of a β-amyloid plaque.

Therefore, the inventors also contemplate a method of producing a $^{11}$C or $^{18}$F labeled compound for PET imaging that comprises a step of reacting (most preferably in an alkylation or acylation of the nitrogen atom in $R_1$ or $R_2$) a compound having a structure of Formula Ia with a $^{11}$C or $^{18}$F labeled alkylating or acylating agent to produce a reaction product

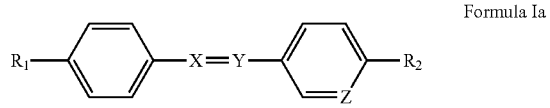

Formula Ia in which X is CH or N, in which Y is CH or N, or in which X and Y together are C(O)NH, and in which Z is CH or N. Most preferably, $R_1$ is $NR_3R_4$ or $OR_5$, $R_2$ is $NR_3R_4$, halogen, halogen isotope, O-heteroaryl, or $NR_3$-heteroaryl, and $R_3$ is H. $R_4$, and $R_5$ are independently H, lower alkyl, O-alkyl; or C(O)-alkyl. In another step, the reaction product is then separated from the $^{11}$C or $^{18}$F labeled alkylating or acylating agent.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

Prior Art FIGS. 1A-1C show the chemical structures of various known imaging agents with PET detectable label.

FIG. 2A depicts an exemplary $^{11}$C-labeled azo-derivative, while FIG. 2B depicts an exemplary $^{11}$C-labeled olefinic derivative.

FIG. 3A depicts an exemplary $^{18}$F-labeled azo-derivative, while FIG. 3B depicts an exemplary $^{18}$F-labeled olefinic derivative.

DETAILED DESCRIPTION

Figure 2:
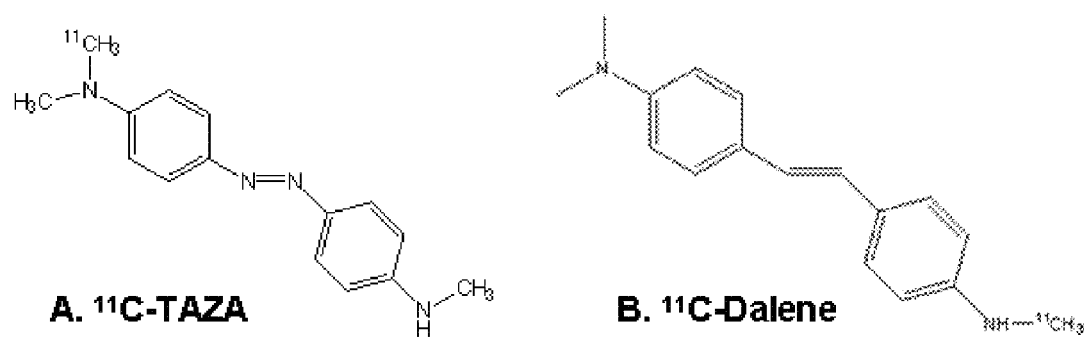
FIGS. 2A-2B show the chemical structures of exemplary imaging agents with PET detectable label according to the inventive subject matter.

The inventors have discovered that selected compounds, and especially substituted and isotope labeled 4,4'-diaryl compounds can be employed as labeling and/or treatment agents for neural diseases that are characterized by the presence of β-amyloid plaques and/or neurofibrillary tangles. Most preferably, where the compounds are used for diagnostics, compounds according to the inventive subject matter will be labeled, typically with a PET-detectable label. On the other hand, it should be noted that the isotope label may be replaced with a corresponding non-isotope atom, particularly where the compound is used as a therapeutic and/or as a prophylactic compound.

In further especially preferred aspects of the inventive subject matter, the compounds will be suitable PET imaging agents for research and early diagnosis of Alzheimer's disease (AD) and are thought to be suitable to establish a relationship between the development of β-amyloid senile plaques, especially in human.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed. Moreover, in some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In other embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. Likewise, the recitation of ranges of values herein is merely intended to serve as a shorthand method of referring individually to each separate value falling within the range. Unless otherwise indicated herein, each individual value is incorporated into the specification as if it were individually recited herein. It should further be noted that all methods described herein can be performed in any suitable order unless otherwise indicated herein or otherwise clearly contradicted by context.

Contemplated Compounds

It is generally contemplated that the compounds of the inventive subject matter will have the general structure of 'substituted amine-(hetero)aryl-linker-(hetero)aryl-substituted amine', and that especially particularly preferred compounds are labeled with a PET-detectable label (e.g., $^{11}$C or $^{18}$F). However, and as already noted above, compounds contemplated herein need not be labeled with a PET detectable label, and suitable alternate labels may be detectable by autoradiography, scintiligraphy, fluorescence microscopy, visual detection (e.g., via precipitating or agglomerating dye), etc. Moreover, it should also be noted that the compounds presented herein need not be labeled at all.

For example, it is contemplated that suitable substituted amine groups in the compounds of the inventive subject matter may be identical or different from each other, and that substituted amine groups may be primary, secondary, or tertiary amines (in some instances even quaternary amines). Suitable substituent will preferably be relatively small (i.e., with molecular weight of less than 200) and lipophilic, however, larger groups and/or hydrophilic groups are not expressly excluded from the scope of the invention. Therefore, suitable amine substituents include mono- and di-substituted amines, in which the substituents are independently H, alkyl, fluoroalkyl, actyl, and/or fluoroacyl, with alkyl typically having between 1 and 6 carbon atoms.

With respect to suitable aryl/heteroaryl moieties it is generally preferred that the aryl or heteroaryl is a five- or six-membered ring with no or between 1-3 heteroatoms, wherein the heteroatom is oxygen, optionally substituted nitrogen, or sulfur. Thus, especially preferred aryl or heteroaryl moieties include benzene, naphthalene, pyridine, quinoline, pyrazine, pyrimidine, quinazoline, triazine, pyrrole, indole, thiphene, benzothiophene, imidazole, pyrazole, oxazole, etc.

With respect to suitable linkers it is generally preferred that the linker has a linear length of between one and six atoms, and most preferably between two and four atoms. While not limiting to the inventive subject matter, suitable linkers will have double bonds to so allow for delocalization of electrons throughout the linker and aromatic ring system. Therefore, especially preferred linkers include olefinic radicals, aza and azo radicals.

In one especially preferred aspect of the inventive subject matter, contemplated labeled compounds will have a structure according to Formula I

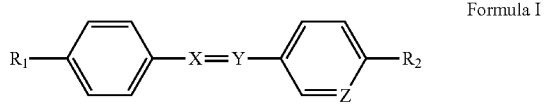

Formula I in which X and Y are independently CH or N, or taken together are C(O)NH, and in which Z is CH or N. With respect to $R_1$ it is preferred that $R_1$ is $NR_3R_4$ or $OR_5$, and it is further preferred that $R_2$ is $NR_3R_4$, halogen, halogen isotope, O-fluoroheteroaryl, or $NR_3$-fluoroheteroaryl. $R_3$, $R_4$, and $R_5$ are independently H, lower alkyl, lower fluoroalkyl, O-alkyl; O-fluoroalkyl; C(O)-alkyl, or C(O)-fluoroalkyl, and it is still further generally preferred that at least one fluorine atom is present in $R_3$, $R_4$, or $R_5$ and is an $^{18}F$ atom, or that at least one carbon atom in $R_3$, $R_4$, or $R_5$ is a $^{11}C$ atom.

In further preferred compounds, the fluorine atom is located in $R_3$, $R_4$, or $R_5$, for example, as $CO(CH_2)_nCH_2{}^{18}F$ or $(CH_2)_nCH_2{}^{18}F$, with n being an integer between 1 and 6. Likewise, it is preferred that the $^{11}C$ atom is located in $R_3$, $R_4$, or $R_5$, for example, in an $^{11}CH_3$ or $(CH_2)_n{}^{11}CH_3$ group, with n being an integer between 1 and 6. While not limiting to the inventive subject matter, it is also preferred that X and Y are both N or both C.

Therefore, especially preferred compounds will have a structure according to Formula II, Formula III, Formula IV, or Formula V (with $R_3$ being $CO(CH_2)_nCH_2{}^{18}F$, or $(CH_2)_nCH_2{}^{18}F$, and with n being an integer between 1 and 6)

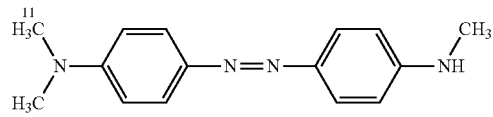

Formula II

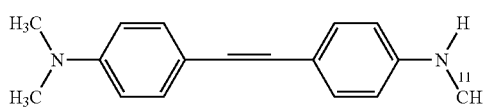

Formula III

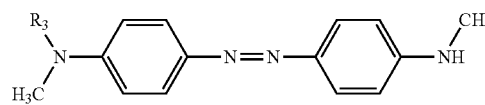

Formula IV

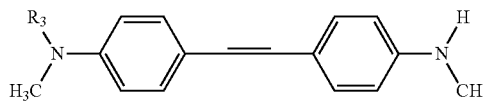

Formula V

Additionally contemplated imaging agents suitable for use herein are disclosed in US 2003/0138374, which is incorporated by reference herein.

The term "alkyl" as used herein refers to a cyclic, branched, or straight hydrocarbon in which all of the carbon-carbon bonds are single bonds, and the term "lower alkyl" refers to a cyclic, branched, or straight chain alkyl of one to ten carbon atoms (e.g., methyl, ethyl, n-propyl, i-propyl, n-butyl, t-butyl, i-butyl (or 2-methylpropyl), cyclopropylmethyl, i-amyl, n-amyl, hexyl, etc.). The term "cycloalkyl" as used herein refers to a cyclic or polycyclic alkyl group containing 3 to 15 carbons. For polycyclic groups, these may be multiple condensed rings in which one of the distal rings may be aromatic (e.g., indanyl, tetrahydronaphthalene, etc.). As still further used herein, the term "alkoxy" refers to a —OR group, wherein R is lower alkyl, substituted lower alkyl, acyl, aryl, substituted aryl, arylalkyl, substituted arylalkyl, heteroarylalkyl, cycloalkyl, substituted cycloalkyl, cycloheteroalkyl, or optionally substituted cycloheteroalkyl.

Furthermore, the term "aryl" refers to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl). Similarly, the terms "heterocycle" or "heterocyclic ring" are used interchangeably herein and refer to a saturated, partially or entirely unsaturated, or aromatic carbocyclic group having a single ring (e.g., morpholino, pyridyl or furyl) or multiple condensed rings (e.g., naphthpyridyl, quinoxalyl, quinolinyl, or indolizinyl) which include at least one heteroatom within the ring(s). The term "heteroatom" as used herein refers to an atom other than carbon (e.g., S, O, or N), which can optionally be substituted with, e.g., hydrogen, halogen, lower alkyl, alkoxy, lower alkylthio, trifluoromethyl, amino, amido, carboxyl, hydroxyl, aryl, aryloxy, heterocycle, heteroaryl, substituted heteroaryl, nitro, cyano, alkylthio, thiol, sulfamido and the like.

Still further, the term "substituted" as used herein means that a hydrogen atom that is covalently bound to a group or atom (or a free electron pair or electron pair of a double bond of an atom) is replaced by a covalently bound non-hydrogen substituent, including hydroxyl, thiol, alkylthiol, halogen, alkoxy, amino, amido, nitro, carboxyl, cycloalkyl, heterocycle, cycloheteroalkyl, acyl, carboxyl, aryl, aryloxy, heteroaryl, arylalkyl, heteroarylalkyl, alkyl, alkenyl, alknyl, and cyano.

It should further be recognized that the compounds contemplated herein may also be active and/or prepared as a metabolites, as prodrugs, and/or otherwise modified compound, wherein the metabolite, prodrug, or modified compound exhibits higher permeability across the blood brain barrier or less toxicity as compared to the unmodified compound and wherein the prodrug or modified compound is converted within the target cell/organ/structure back into the unmodified form. For example, conversion of contemplated compounds into prodrugs may be useful where the active drug is too toxic for safe systemic administration, or where the contemplated compound is less rapidly transported across the blood brain barrier, or where the body breaks down the compound before reaching its target. Contemplated compounds may also be transformed by the hepatic phase I and/or phase II enzyme system, or by gastric acidity, intestinal microbial environment, or other biochemical process. Thus, suitable compounds may be oxidized, hydroxylated, ligated to a carbohydrate, etc. Similarly, contemplated compounds may be formulated such as to facilitate transport across the blood brain barrier, and all known formulations are deemed suitable for use herein.

Contemplated Compositions

Based on the observed and/or expected improved solubility and specificity of compounds contemplated herein, it should be recognized that these compounds may be employed for various pharmaceutical, diagnostic, and research uses. Among other uses, it is contemplated that the compounds will allow early diagnosis of formation of senile plaques and/or neurofibrillary tangles, and will allow to more precisely locate and even quantify such plaques and tangles. In still further contemplated aspects, it is also thought that the compounds presented herein may be employed to reduce or even prevent formation of senile plaques and/or neurofibrillary tangles. Additionally, the inventors have discovered that the compounds presented herein specifically bind to norepinephrine transporters (NET) and are thought to be taken up into a cell via the NET, and that such specific binding/uptake may be used for diagnostic and therapeutic uses for disorders or conditions associated with NET. Thus, it is contemplated that the compounds and compositions according to the inventive subject matter are suitable for diagnostic and/or therapeutic (including prophylactic) purposes.

Consequently, a pharmaceutical composition may include at least one of contemplated compounds (preferably in oral or parenteral formulation) at a concentration effective to treat a disease or condition associated with (a) development of presence of senile plaques and/or neurofibrillary tangles, or (b) NET. Compounds in such compositions will typically not be labeled. On the other hand, compounds in diagnostic compositions will preferably be labeled with a PET detectable label (e.g., $^{11}C$ or $^{18}F$) at a specific activity that allows in vivo acquisition of a signal. Consequently, pharmaceutical or diagnostic compositions comprising compounds presented herein are especially contemplated, typically comprising a pharmaceutically acceptable carrier. Similarly, methods of imaging or treating (including prophylactic treatment) a neural disorder in a subject are contemplated in which compositions comprising compounds presented herein are administrated at a dosage effective to image or treat the disorder. For example, contemplated methods of diagnosing a mammal having a disease or condition that is associated with senile plaques and neurofibrillary tangles include a step in which contemplated compounds are administered to the mammal (typically in a labeled form) at a dosage effective to locate and/or quantify in vivo binding of the labeled compound to the senile plaques and/or neurofibrillary tangles. In another example, contemplated methods of diagnosing a mammal having a disease or condition that is associated with a dysfunction, lack, or over-expression of NET include a step in which contemplated compounds are administered to the mammal (typically in a labeled form) at a dosage effective to locate and/or quantify in vivo binding of the labeled compound to the NET (and/or uptake via NET).

Preferably, the label is an isotope suitable for detecting the compound in vivo using PET (most preferably $^{18}F$), and contemplated compounds are typically parenterally administered. Viewed from a different perspective, compositions comprising contemplated compounds will be useful in the treatment, prevention, diagnosis and/or therapeutic follow-up of Alzheimer's disease, minimal cognitive impairment, dementia, inflammation associated with these neurological processes, inflammation as a result of other injuries, or pathophysiologies related to cancer, or will be useful in the treatment, prevention, diagnosis and/or therapeutic follow-up of certain neural (e.g., ADHD) or metabolic disorders (e.g., obesity) associated with a dysfunction, lack, or over-expression of NET.

Particularly preferred compositions according to the inventive subject matter may be administered using various routes, including orally, parenterally, by inhalation, topically, rectally, nasally, or via an implanted reservoir, wherein the term "parenteral" as used herein includes subcutaneous, intravenous, intramuscular, intrathecal, intralesional, and intracranial administration (typically injection or infusion). Preferably, the compositions are administered orally, intraperitoneally, or intravenously. Such compositions are prepared according to techniques well-known in the art of pharmaceutical formulation and may be prepared as solutions in saline, employing benzyl alcohol or other suitable preservatives, absorption promoters to enhance bioavailability and/or transport across the blood-brain barrier, fluorocarbons, and/or other conventional solubilizing or dispersing agents.

With respect to the amount of contemplated compounds in the composition, it should be recognized that the particular quantity will typically depend on the specific formulation, particular compound, and desired purpose. Therefore, it should be recognized that the amount of contemplated compounds will vary significantly. However, it is generally preferred that the compounds are present in a minimum amount effective to deliver a therapeutic effect and/or to be visualized in vitro and/or in vivo.

Thus, in most preferred embodiments, contemplated compounds will be present in a liquid carrier (single solvent or complex solvent system, preferably monophasic) in amount of between about 0.1 µg/ml to about 500 mg/ml, more typically in an amount of between about 10 µg/ml to about 100 mg/ml, and most typically between about 1 µg/ml to about 10 mg/ml. Where the formulation is a solid, contemplated compounds will be present in an amount of between about 0.1 µg/g to about 900 mg/g, more typically in an amount of between about 10 µg/g to about 500 mg/g, and most typically between about 1 mg/g to about 200 µg/g. With respect to a dosage unit, it is generally contemplated that contemplated compounds are administered at a dosage effective to achieve a desired therapeutic effect or at a dosage effective to provide visualization in vitro and/or in vivo. Therefore, suitable amounts of contemplated compounds will be in the range of 0.1 µg per dosage unit to about 0.5 gram per dosage unit, more typically between 10 µg per dosage unit to about 0.05 gram per dosage unit, and most typically between 50 µg per dosage unit to about 100 mg per dosage unit. Thus, suitable dosages will be in the range of about 0.1 µg/kg and 10 mg/kg, more typically between 1 µg/kg and 5 mg/kg, and most typically between 10 µg/kg and 1 mg/kg.

With respect to suitable labeling amounts, it is generally contemplated that all quantities are deemed suitable that can be detected using an in vitro and/or in vivo imaging technology, and particularly in vivo PET. Typically, a radiolabeling precursor compound will be labeled with a fluorine-18 source by an imaging center. For example, several microcuries to several millicuries will be produced and then used for imaging studies. Therefore, contemplated compounds and kits may also include at least one of a precursor molecule, the labeling molecule containing 18F, and the 18F labeled ligand.

Contemplated Uses

It is generally contemplated that the compounds and compositions presented herein will be particularly useful in imaging and/or diagnostic use of conditions associated with presence of β-amyloid and/or NET. Such imaging and/or diagnostic use is preferably performed in vivo, but in vitro use is also expressly contemplated. Moreover, due to specific binding and/or uptake of contemplated compounds, therapeutic and/or prophylactic use are also deemed suitable uses. For example, suitable uses especially include treatment of various attention deficit disorders, and/or treatment of depression, schizophrenia, and numerous other mood disorders.

Experimental Data

The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

In selected experiments, and as further more specifically noted below, the synthesized compounds were evaluated in human post mortem brain tissue that were fresh frozen cryostat sectioned AD brain slices for comparison to age and gender-matched control slices. Brains with a range of AD pathology were selected based upon Braak and Braak staging and based upon clinical scores from the mini mental state examination. As can be seen from the data below, contemplated compounds have enhanced affinity for the amyloid plaques, which is expected to translate to higher SUVR values, thus making measurement of changes between HC, MCI and AD more precise. In particular, the effectiveness of a 4-$^{11}$C-methylamino-4'-dimethylamino-azobenzene ($^{11}$C-TAZA) and 4-$^{11}$C-methylamino-4'-(N,N-dimethylamino) stilbene ($^{11}$C-Dalene) was evaluated for binding to the SP sites in the hippocampus region of the human brain (AD and control). Binding of $^{11}$C-TAZA and $^{11}$C-Dalene was compared with $^{11}$C-PIB.

Radiosynthesis was carried out by reacting 4-amino-4'-dimethylaminoazobenzene or 4-amino-4'-(N,N-dimethylamino)stilbene (1 mg/0.5 cc acetone) with $^{11}$C-methyltriflate prepared in the GE FXCPro. $^{11}$C-Methyltriflate was trapped at −20° C. and subsequently heated for 5 mins at 80° C. $^{11}$C-TAZA and $^{11}$C-Dalene were purified using HPLC using 60% acetonitrile and 0.1% triethylamine, and the flow rate was 2.5 ml/min. Results suggest that $^{11}$C-TAZA and $^{11}$C-Dalene are effective imaging agents due to their binding capabilities in the hippocampus of AD patients. In vivo evaluation of $^{11}$C-TAZA and $^{11}$C-Dalene has been carried out as described further below.

Figure 3A:
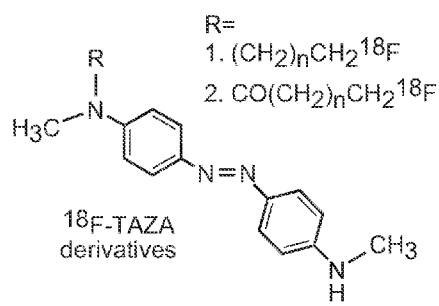
FIGS. 3A-3B show the chemical structures of exemplary imaging agents with PET detectable label according to the inventive subject matter.
Figure 3B:
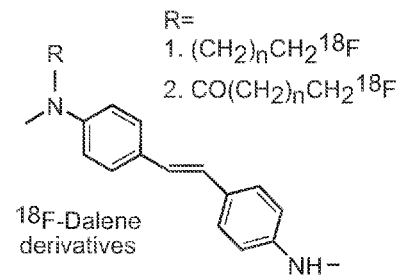
Figure 6:
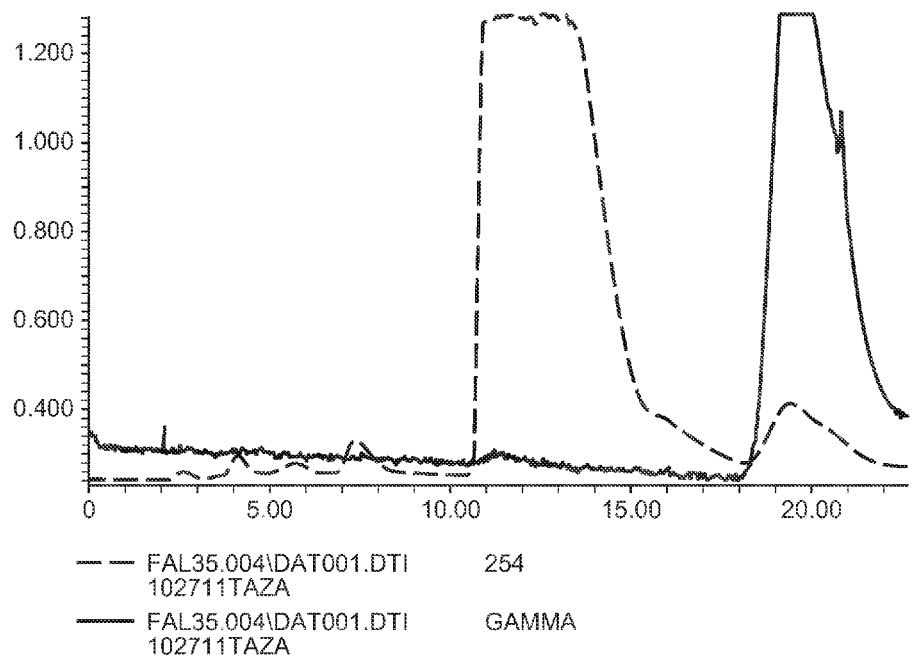
FIG. 6 depicts an exemplary HPLC elution profile of an alkylation reaction with $^{11}$C-TAZA appearing at 19-20 minutes retention time.

Radiolabeling was carried out with high specific activity fluorine-18 which is routinely prepared in the MC-17 Scandotronix cyclotron via the $^{18}$O(p, n)$^{18}$F reaction. Radiosynthesis of $^{18}$F-TAZA derivatives and $^{18}$F-Dalene analogs (FIGS. 3A and 3B) has been carried out in two steps, the first step is the $^{18}$F-fluoride nucleophilic displacement to provide the $^{18}$F-fluoroalkyl and $^{18}$F-fluoroacyl synthons using reported procedures. The second step is the $^{18}$F-fluoroalkylation/$^{18}$F-fluoroacylation of the aniline nitrogen. The product mixtures were purified by HPLC, and FIG. 6 shows a typical elutionprofile with $^{11}$C-TAZA appearing at 19-20 minutes retention time.

Measurement of affinity of compounds for amyloid plaques and NFT: Binding affinity of the compounds have been measured using human brain slices and tissue homogenates. Both transgenic mice brain slices and human brain slices will be used in order to ascertain characteristics of the compounds across species. Autoradiographic studies have been carried out by using either tritiated, carbon-11 or fluorine-18 labeled reference compounds. In the case of mice brains, either sagittal or horizontal sections will be used. For human brains, hippocampus and frontal cortex were used. In vitro autoradiography studies with $^3$H-PIB will be performed on 7 micron slices of hippocampus of AD patients (n=2) and control brains (n=2). Hippocampus slices will be incubated with the radiotracer in 40% ethanol-water for 1 hour. Slices will then washed with cold water, 70%-70%-70% alcohol, and water for 2, 1, 1, 1, 1 mins, respectively. $^3$H-PIB bound specifically to SP present in AD brains was compared to the normal controls and at different drug concentrations. Non-specific binding was assessed using 10 µM PIB. The slides were air dried and apposed to phosphor screens overnight and read by the Cyclone Phosphor Imaging System (Packard Instruments Co). The amount of bound compounds in the autoradiograms will be evaluated in various brain regions (as digital lights units (DLU]/mm$^2$) using the OptiQuant acquisition and analysis program (Packard Instruments Co). Data was analyzed using following procedure: (1) the non-specific binding of $^3$H-PIB was subtracted for all samples; (2) the specific binding was normalized to 100% (no competitive ligand) and (3) the binding isotherms were fit to the Hill equation (KELL BioSoft software (v 6), Cambridge, U.K.). The K$_i$ was calculated by the Cheng-Prussof equation using the reported Kd value, for $^3$H-PIB.

Using human Alzheimers brain homogenate tissue in 10% alcohol in PBS buffer and $^3$H-PIB, the binding affinity (IC$_{50}$) for TAZA was found to be 12.8 nM compared to PIB which was 100 nM. Thus, TAZA is potentially 10 times better in binding to amyloid plaques in the human brain tissue compared to PIB.

In Vitro Autoradiographic Studies: Plaque imaging with $^{11}$C-PIB: In vitro studies using $^3$H-BTA-1 (an analog of 11C-PIB) on post mortem AD brain slices indicated selective binding to β-amyloid deposits. Binding studies with $^{11}$C-PIB were carried out using modifications of described procedures. Brain sections will be incubated for 20-40 mins at 37° C. with $^{11}$C-PIB at a concentration of 5-10 µCi/cc 40% alcohol. After incubation the sections will be washed with cold 70% alcohol thrice followed by a cold water rinse. The sections will then be air dried and apposed to phosphor screens overnight and read by the Cyclone Phosphor Imaging System (Packard Instruments Co). The amount of bound $^{11}$C-PIB in the autoradiograms will be evaluated in various brain regions (as digital lights units (DLU]/mm$^2$) using the OptiQuant acquisition and analysis program.

Human post-mortem Studies: We used post mortem human brain specimens from the UCI-ADRC Brain tissue repository for in vitro experiments. Age and gender matched AD brain and control brain tissue were used. Control cases consisted of clinically assessed nondemented individuals ranging in age from 70-90 years of age. AD brain samples were selected for end-stage pathology (based upon comments by the neuropathologist and Braak & Braak stage of VI. We matched each AD case with a similarly aged control case. AD cases, were selected on the basis as having a clinic visit within 1 year of death. Frozen hippocampus and frontal cortex, regions vulnerable to AD pathology, were selected for these studies. Sections of the cerebellum were used as a measure of low/nonspecific binding. Chunks of frozen tissue were dissected for immunohistochemical and autoradiographic techniques, as well as for biochemical experiments.

Serial cryostat sections at 5-10 µm were used. The first set of sections was used to establish the extent of senile plaque and neurofibrillary tangle formation using immunohistochemistry and histological techniques. Antibodies against Aβ1-16, Aβ1-40 and Aβ1-42 were used to detect Aβ.

Figure 4:
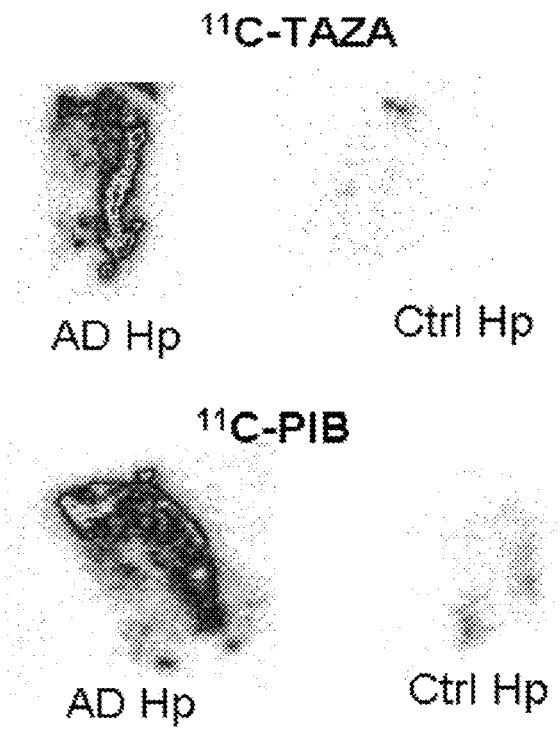
FIG. 4 exemplarily illustrates differences in imaging of human hippocampus sections of an AD patient sample and a normal control sample using $^{11}$C-TAZA versus the known imaging compound $^{11}$C-PIB.

Senile Plaque Imaging: Binding of $^{11}$C-TAZA was compared with $^{11}$C-PIB. In vitro autoradiography studies were performed on 7 micron slices of hippocampus of AD patients (n=2) and control brains (n=2). Hippocampus slices were incubated with the radiotracer (10-25 µCi/cc) in 40% ethanol-water for ½ hour. Slices were then washed with cold water, 70%-70%-70% alcohol, and water for 2,1,1,1,1 mins, respectively. $^{11}$C-PIB was studied similarly. Dried slides were exposed on to phosphor screens and slides were visualized by Optiquant image analysis program and binding evaluated as Digital light units/mm$^2$ (DLU/mm2) were measured. $^{11}$C-TAZA bound specifically to SP present in AD brains compared to the normal controls. AD/Control hippocampus ratios was >100. In the case of $^{11}$C-PIB, AD/Control hippocampus ratio>5. Non-specific binding was assessed using 10 µM PIB. Displacement of $^{11}$C-TAZA by PIB was >80%, suggesting similar binding site for $^{11}$C-TAZA and $^{11}$C-PIB. These studies suggest that $^{11}$C-TAZA is an effective imaging agent due to its binding capabilities in the hippocampus of AD patients. In vivo evaluation of $^{11}$C-TAZA is in progress. Results are shown in FIG. 4 depicting human hippocampus sections of AD patient and normal control showing binding of $^{11}$C-TAZA and $^{11}$C-PIB. Little binding is seen in the normal controls for both radiotracers.

Figure 5:
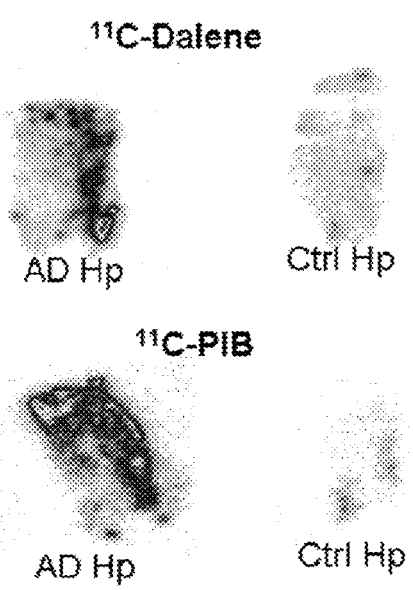
FIG. 5 exemplarily illustrates differences in imaging of human hippocampus sections of an AD patient sample and a normal control sample using $^{11}$C-Dalene versus the known imaging compound $^{11}$C-PIB.

[11]C-Dalene bound specifically to SP present in AD brains compared to the normal controls. AD/Control hippocampus ratios was >5. In the case of $^{11}$C-PIB, similar results were observed-AD/Control hippocampus ratio>5. Non-specific binding was assessed using 10 µM PIB. Displacement of [11]C-Dalene by PIB was not complete, with a significant amount of [11]C-Dalene remaining bound to the SP. These studies suggest that [11]C-Dalene is an effective imaging agent due to its binding capabilities in the hippocampus of AD patients. In vivo evaluation of [11]C-Dalene is in progress. FIG. 5 depicts human hippocampus sections of AD patient and normal control showing binding of [11]C-Dalene and $^{11}$C-PIB. Little binding is seen in the normal controls for both radiotracers.

Figure 7:
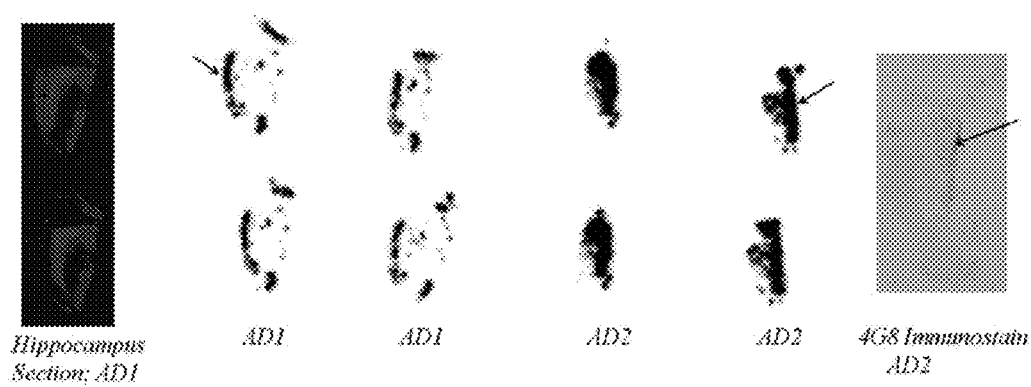
FIG. 7 depicts exemplary results of human hippocampus sections of two Alzheimer's disease patients (AD1, AD2) showing binding of $^{11}$C-TAZA, which correlates to immunostained beta-amyloid plaques.
Figure 8:
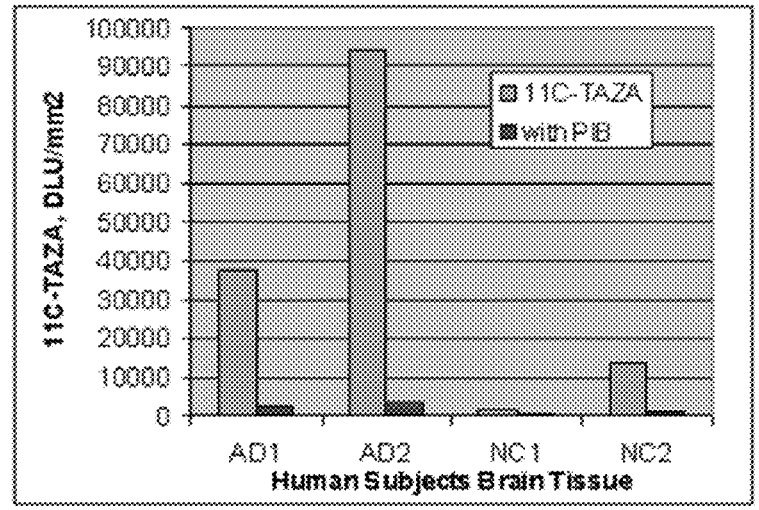
FIG. 8 is a graph depicting test results of a comparison between $^{11}$C-TAZA and $^{11}$C-PIB binding in normal/control and Alzheimer's disease neural tissue.

Based on these findings, it should be noted that $^{11}$C-TAZA exhibited a higher specific binding component compared to both [11]C-Dalene and $^{11}$C-PIB. It is therefore also expected that the fluorine-18 analogs of both TAZA and Dalene will exhibit significant affinity for the human senile plaques. FIG. 7 depicts human hippocampus sections of two AD patients showing binding of $^{11}$C-TAZA which correlates to immunostained beta-amyloid plaques, and FIG. 8 depicts a graph showing a comparison of $^{11}$C-TAZA and $^{11}$C-PIB binding in humans (normal and Alzheimer's disease).

Based on earlier experimental observations (not shown), the inventors contemplated that the compounds presented herein not only bind with high specificity to β-amyloid, but also with similar high specificity to the NET. To investigate binding to/uptake by the NET, the effect of atomoxetine (ATX, a selective norepinephrine reuptake inhibitor) on the kinetics of Dalene and TAZA was tested. More specifically, Sprague-Dawley rats (308-468 g) received two 90 min PET scans each on two separate days (1-4 weeks apart) with an Inveon scanner. On first day each rat received a baseline scan, one with $^{11}$C]Dalene and the other with $^{11}$C]TAZA (96±8 MBq). The second day each animal was pre-injected i.v. with a 50 µl bolus of ATX (1-2 mg/Kg), 17 min before $^{11}$C]Dalene and 2 min before $^{11}$C]TAZA (33±7 MBq). The images were reconstructed dynamically in 25 frames (4×0.5 min, 8×1 min, 5×2 min, 2×5 min, 6×10 min). Each subject received a CT scan that was used for attenuation and scatter correction. Images were normalized to Paxinos & Watson space via co-registration with an MR rat template. Common regions of interest were drawn on the MR template and placed on brainstem, thalamus (Tha), and midbrain (Mid), brain regions with highest uptake as well as anterior cingulate cortex area 1 (Cg1), region with low NET density and which was chosen as a reference based on previous studies. Time activity curves (TACs) from all regions were analyzed in PMOD using Logan non-invasive method with Cg1's k2' parameter estimated by fitting of brainstem data to MRTM.

Figure 11:
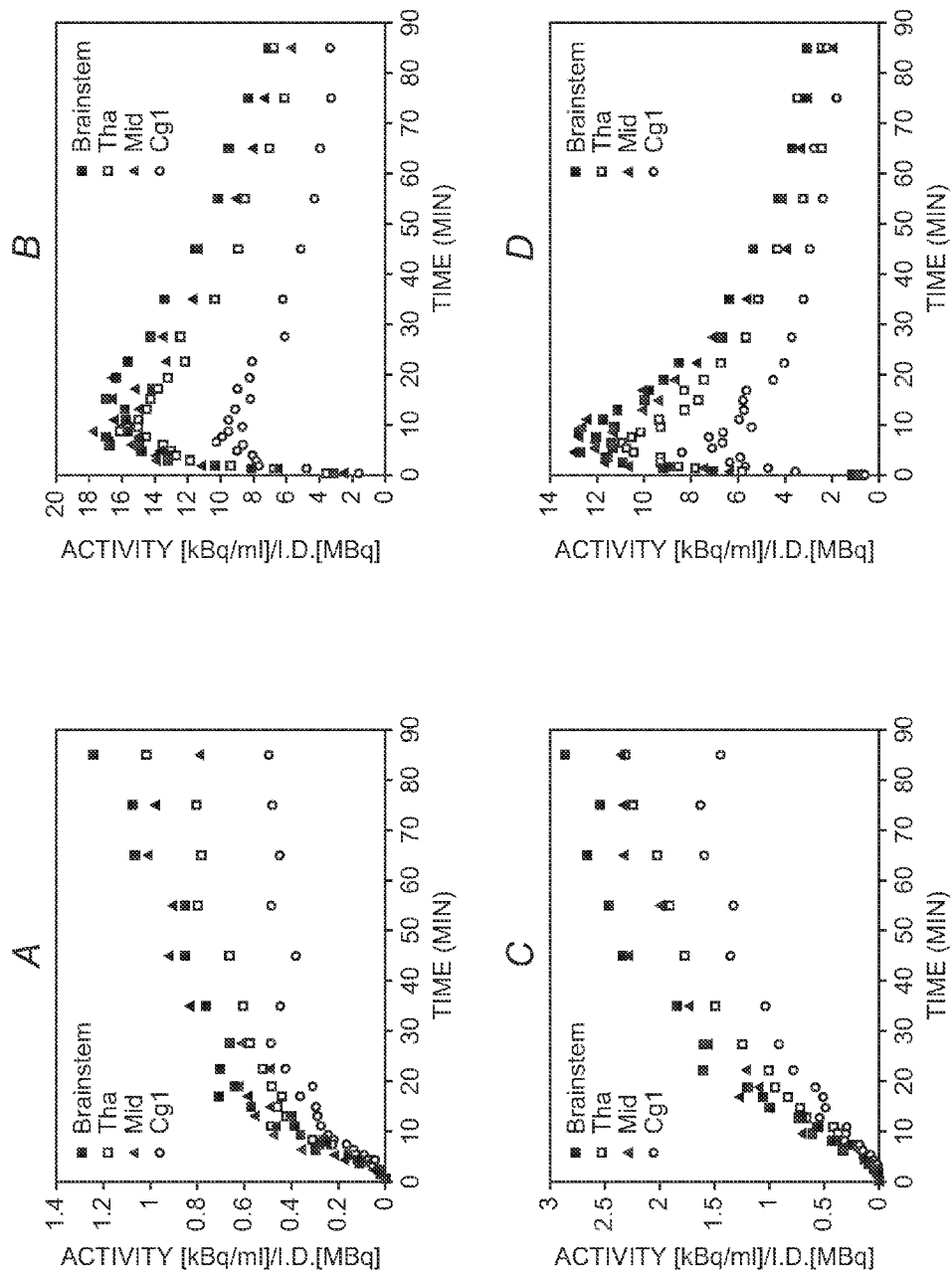
FIG. 11 depicts kinetic of binding/uptake of selected compounds to/by NET using atomoxetine, a selective norepinephrine reuptake inhibitor.

FIG. 11 shows time activity curves for normalized $^{11}$C]Dalene TACs from baseline and atomoxetine (ATX) condition, respectively (A and B). Similarly, $^{11}$C]TAZA TACs are presented in C and D. As can be readily taken from the graphs, in the baseline condition both kinetics were slow and the ratio target/reference reached a constant level at 20 min post tracer injection. The kinetics in ATX condition were much faster and with a peak uptake 14-fold higher than in the control for $^{11}$C]Dalene in the brainstem and 5-fold for $^{11}$C]TAZA. [11]C]Dalene baseline BPND values were 1.42 (brainstem), 0.86 (Tha), 0.91 (Mid) with changes in $BP_{ND}$ of −18% (brainstem), −12% (Tha), and 5.4% (Mid) in ATX condition. [11]C]TAZA baseline BPND values were 0.7 (brainstem), 0.41 (Tha), 0.50 (Mid) with increases in $BP_{ND}$ of 11% (brainstem), 6% (Tha), and 18% (Mid) in ATX condition.

As can be seen, $^{11}$C]Dalene and $^{11}$C]TAZA binding patterns were consistent with the expected NET distribution in the rat brain. [11]C]Dalene binding values were higher than those of $^{11}$C]TAZA. Atomoxetine pre-injection promoted a large and fast increase in $^{11}$C]Dalene and $^{11}$C]TAZA brain uptake. This effect could be attributed to systemic effects of excess norepinephrine caused by the large ATX dose, which generated an increase in blood flow and possibly changes in tracer free fraction.

Binding to norepinephrine transporters (NET) were further evaluated in normal rats using PET/CT. Radiosynthesis was carried out by reacting 4-amino-4'-dimethylaminoazobenzene (1 mg/0.5 cc acetone for $^{11}$C-TAZA) and 4-methylamino-4'-(N-methylamino)stilbene (1 mg/0.5 cc acetone for [11]C-Dalene) with 11C-methyltriflate prepared in the GE FXCPro synthesis unit. [11]C-Methyltriflate was trapped at −20° C., subsequently heated for 5 mins at 80° C. and purified using HPLC. In vitro autoradiography studies were performed on 7 micron slices of hippocampus of AD patients and control brains. Slices were incubated with the radiotracer (10-25 bCi/cc, $^{11}$C-TAZA, [11]C-Dalene or $^{11}$C-PIB) in 40% ethanol-water for ½ hour. Non-specific binding was assessed using 10 bM PIB for the 3 tracers.

Figure 9:
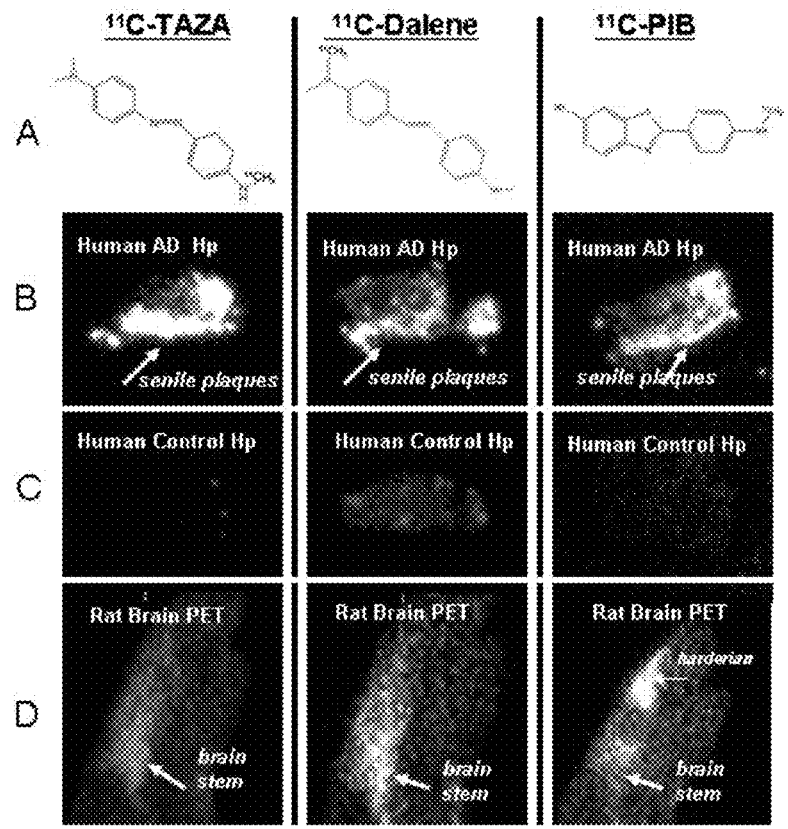
FIG. 9 depicts results for binding of $^{11}$C-TAZA, $^{11}$C-Dalene, and $^{11}$C-PIB to human brain hippocampal sections (A and B) and in vivo rat brain sagittal sections (C).

Slices were then washed and exposed on to phosphor screens and slides were analysed by Optiquant image analysis program for SP binding Digital light units/mm$^2$ (DLU/mm$^2$). Sprague-Dawley rats were scanned after IV injection of $^{11}$C-TAZA and [11]C-Dalene in Inveon PET/CT and displacement studies were done with atomoxetine (1 mg/kg). PET images were analyzed using PMOD. Results: $^{11}$C-TAZA, $^{11}$C-Dalene and $^{11}$C-PIB were obtained in 25 to 100 mCi yields in specific activities >1000 Ci/mmol. The radiosynthesis was clean with >95% radiochemical product for each of them. $^{11}$C-TAZA and $^{11}$C-Dalene bound specifically to SP present in AD brains compared to the normal controls as shown in FIG. 9. AD/Control hippocampus ratios were: $^{11}$C-TAZA>30; $^{11}$C-Dalene>5 and $^{11}$C-PIB>5. Presence of SP in the AD brains were confirmed using 4G8 antibody immunostaining for Aβ-amyloid. The control brains exhibited little or no SP. Unlabeled PIB displaced $^{11}$C-TAZA and $^{11}$C-Dalene, suggesting similar binding sites. $^{11}$C-TAZA and $^{11}$C-Dalene also exhibited selective binding/uptake in NET brain regions such as brain stem and thalamus. Ratios of brain stem to cingulate gyms (used as reference region) was >2. Atomoxetine reduced the binding of both $^{11}$C-TAZA and $^{11}$C-Dalene with the former showing greater reduction.

FIG. 9 depicts results for binding of $^{11}$C-TAZA, $^{11}$C-Dalene, $^{11}$C-PIB: Chemical structures (A); Binding to postmortem human AD brain hippocampal sections, in vitro autoradiographs (B); Binding to postmortem human control brain hippocampal sections, in vitro autoradiographs (C); Binding to normal rat brain sagittal sections, in vivo PET (D). These studies suggest that $^{11}$C-TAZA and $^{11}$C-Dalene are effective imaging agents for human SP in AD patients. Of the 3 radiotracers, $^{11}$C-TAZA showed the highest binding to SP. Our studies also suggest that $^{11}$C-TAZA and $^{11}$C-Dalene bind to/are taken up by NET in human.

In still further experiments, binding/uptake of contemplated compounds to/by NET was investigated in adipose tissue, and especially brown adipose tissue. It should be appreciated that due to the innervation of brown adipose tissue (BAT) with neurotransmitter, norepinephrine is essential for regulation of thermogenesis, and thus has a role in obesity and diabetes. Norepinephrine acts by activating β3-adrenoceptor to increase BAT metabolic activity measurable using $^{18}$F-FDG PET. Norepinephrine transporter (NET) inhibitors such as atomoxetine play an important role in BAT activity by increasing norepinephrine levels. Therefore imaging NET along with glucose metabolism in BAT will provide useful tools to measure mass and activity of adipose tissue and especially BAT.

Male Sprague-Dawley rats were fasted for 24 hrs prior to $^{18}$F-FDG administration. Rats were administered i.v. ~0.3 mCi $^{18}$F-FDG under 2% isoflurane anesthesia. The same rats were treated with atomoxetine 1 mg/kg, 30 mins before $^{18}$F-FDG administration. Rats were awake for 60 mins and subsequently anesthetized for upper-body Inveon MicroPET/CT scan. To evaluate whether enhanced $^{18}$F-FDG uptake in activated BAT could be reduced by pharmacologic interventions, propranolol (β3-adrenorecptor inhibitor) 5 mg/kg was given intraperitoneally in anesthetized rats, 30 minutes prior to atomoxetine administration. For NET imaging, $^{11}$C-TAZA (4-$^{11}$C-methylamino-4'-dimethylaminoazobenzene) and $^{11}$C-Dalene (4-methylamino-4'-(N—$^{11}$C-methyl-N-methylamino)stilbene) were administered iv (~0.5-3 mCi) and scanned in Inveon PET/CT for 90 mins. Competition studies were done with atomoxetine (preinjection, 1-2 mg/kg). PET/CT data was analysed using IRW and PMOD.

Figure 10:
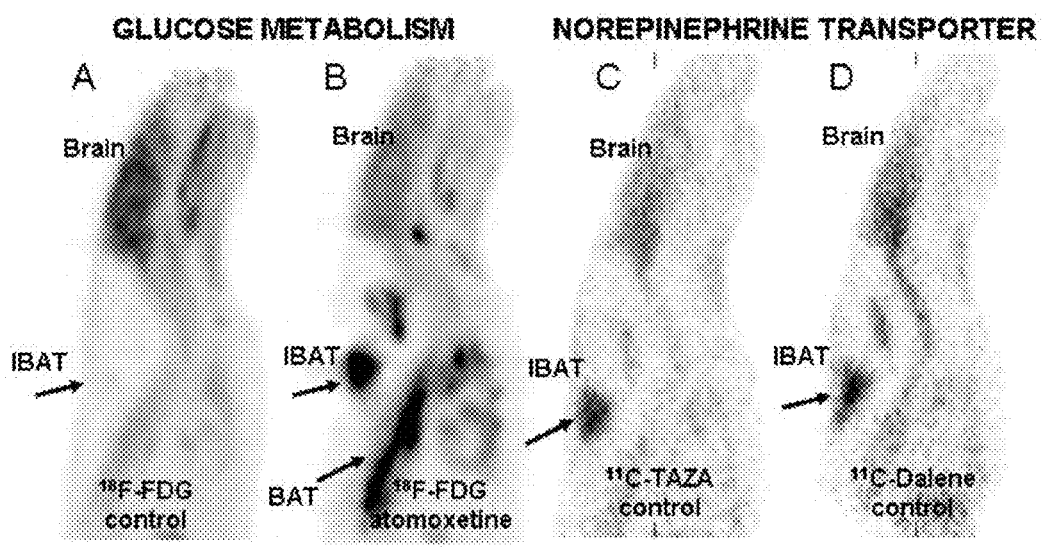
FIG. 10 depicts results for binding/uptake of selected compounds to/by NET in adipose tissue.

Atomoxetine increased the average $^{18}$F-FDG uptake of IBAT significantly, >15 times, compared to controls (365±170 vs. 23.9±8.7 kBq/cc) as can be seen from FIG. 10. This is consistent with blocking of NET by atomoxetine and increasing norepinephrine. Propranolol (adrenergic receptor inhibitor) reduced the average $^{18}$F-FDG uptake of IBAT significantly. Interscapular BAT (IBAT) was clearly visualized with both $^{11}$C-TAZA and $^{11}$C-Dalene with IBAT to reference muscle ratios >4. Atomoxetine reduced IBAT binding of both $^{11}$C-TAZA and $^{11}$C-Dalene by 60% and 35%, respectively. Incomplete displacement may be due to possible internalization of the radiotracers. Although there was similarity in the different BAT regions visualized by atomoxetine stimulated $^{18}$F-FDG uptake and NET agents $^{11}$C-TAZA and $^{11}$C-Dalene, $^{18}$F-FDG uptake appeared more prominent. Autoradiography of IBAT and white adipose tissue (WAT) confirmed the data obtained by PET. FIG. 10 illustrates $^{18}$F-FDG uptake in control rat (A); $^{18}$F-FDG uptake in rat after preinjection of atomoxetine showing activation of BAT (B, arrows showing interscapular BAT); $^{11}$C-TAZA showing NET binding/uptake in BAT (C, arrows showing interscapular BAT); $^{11}$C-Dalene showing NET binding/uptake in BAT (D, arrows showing interscapular BAT).

These studies suggest that $^{11}$C-TAZA and $^{11}$C-Dalene are effective imaging agents for NET in adipose tissue, and especially BAT. Atomoxetine increases norepinephrine in BAT resulting in hypermetabolic effects measurebale by $^{18}$F-FDG uptake at ambient temperature in the rodent model. Correlation of NET binding/uptake of $^{11}$C-TAZA and $^{11}$C-Dalene and $^{18}$F-FDG uptake in various BAT regions is underway in order to assess the quantitative relationship of NET concentration with metabolic activity.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A compound having a structure according to Formula I:

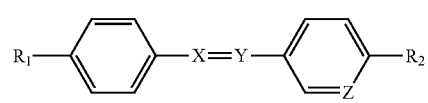

Formula I wherein X is CH or N, wherein Y is CH or N, or wherein X and Y together are C(O)NH, and wherein Z is CH or N; wherein $R_1$ is $NR_3R_4$; and wherein $R_2$ is $NHR_4$; wherein $R_3$ is a C(O)-fluoroalkyl, and —$R_4$ is a lower alkyl; and wherein fluoroalkyl is selected form the group consisting of $(CH_2)_nCH_2F$ and $(CH_2)_nCH_2{}^{18}F$, and n is an integer between 1 and 6.

2. The compound of claim 1 wherein the fluoroalkyl is $(CH_2)_nCH_2{}^{18}F$.

3. The compound of claim wherein X and Y are both N or both C.

4. The compound of claim 1 having a structure according to Formula IV or Formula V

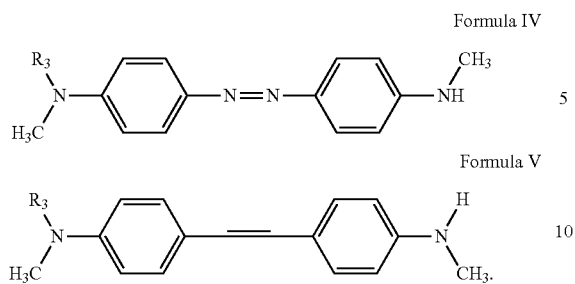

wherein $R_3$ is a C(O)-fluoroalkyl, wherein fluoroalkyl is $(CH_2)_n CH_2{}^{18}F$ and n is an integer between 1 and 6.

5. The compound of claim 1 further comprising a pharmaceutically acceptable carrier to form a pharmaceutical composition.

6. The compound of claim 5 wherein the compound is present in the composition in an amount effective to allow PET imaging of a β-amyloid plaque or neurofibrillary tangle in vitro.

7. The compound of claim 5 wherein the compound is present in the composition in an amount effective to allow PET imaging of a β-amyloid plaque or neurofibrillary tangle in vivo.

8. The compound of claim 5 formulated for parenteral administration.

* * * * *